(12) United States Patent
Gardner

(10) Patent No.: US 11,135,197 B2
(45) Date of Patent: Oct. 5, 2021

(54) DOSAGE REGIMEN OF AN S1P RECEPTOR MODULATOR

(71) Applicant: Argentum Pharmaceuticals LLC, New York, NY (US)

(72) Inventor: Jeffrey R. Gardner, New York, NY (US)

(73) Assignee: Argentum Pharmaceuticals LLC, New York, NY (US)

( * ) Notice: Subject to any disclaimer, the term of this patent is extended or adjusted under 35 U.S.C. 154(b) by 0 days.

(21) Appl. No.: 17/168,397

(22) Filed: Feb. 5, 2021

(65) Prior Publication Data

US 2021/0244708 A1 Aug. 12, 2021

Related U.S. Application Data

(60) Provisional application No. 62/971,724, filed on Feb. 7, 2020.

(51) Int. Cl.
| | | |
|---|---|---|
| *A61K 31/397* | (2006.01) | |
| *A61P 25/00* | (2006.01) | |
| *A61K 9/00* | (2006.01) | |
| *A61K 39/25* | (2006.01) | |

(52) U.S. Cl.
CPC .......... *A61K 31/397* (2013.01); *A61K 9/0053* (2013.01); *A61K 39/25* (2013.01)

(58) Field of Classification Search
CPC .............................. A61K 31/397; A61P 25/00
USPC .................................................... 514/210.01
See application file for complete search history.

(56) References Cited

U.S. PATENT DOCUMENTS

| 7,939,519 B2 | 5/2011 | Pan et al. |
|---|---|---|
| 8,486,930 B2 | 7/2013 | De La Cruz et al. |
| 8,492,441 B2 | 7/2013 | Legangneux |
| 9,051,335 B2 | 6/2015 | Umeuchi et al. |
| 10,543,179 B2 | 1/2020 | Boulton et al. |
| 2005/0064516 A1 | 3/2005 | Kantor et al. |
| 2006/0121052 A1 | 6/2006 | Sotelo-Morales et al. |
| 2006/0172338 A1 | 8/2006 | Dotan et al. |
| 2010/0160259 A1 | 6/2010 | Schmouder et al. |
| 2011/0039818 A1 | 2/2011 | Legangneux |
| 2013/0217899 A1 | 8/2013 | Marom et al. |
| 2014/0371323 A1 | 12/2014 | Rane |
| 2017/0027907 A1 | 2/2017 | Legangneux et al. |
| 2017/0304289 A1 | 10/2017 | Smith |
| 2017/0333418 A1 | 11/2017 | Hallak et al. |
| 2019/0262353 A1 | 8/2019 | Yong et al. |

FOREIGN PATENT DOCUMENTS

CA   2 280 061 A1   2/2000

OTHER PUBLICATIONS

International Search Report (PCT/ISA/210) issued in PCT Application No. PCT/US2021/016695 dated Apr. 12, 2021 (three (3) pages).
Written Opinion (PCT/ISA/237) issued in PCT Application No. PCT/US2021/016695 dated Apr. 12, 2021 (three (3) pages).
Harel A., "How I Treat Siponimod for Secondary Progressive Multiple Sclerosis", Neurology Advisor, Sep. 1, 2019, pp. 1-9, Retrieved from https://www.neurologyadvisor.com/expert-perspective/asaff-hare1-md/(nine (9) pages).
Schmouder et al., "FTY720: Placebo-Controlled Study of the Effect on Cardiac Rate and Rhythm in Healthy Subjects", J Clin Pharmacol, 2006, pp. 895-904, vol. 46, (10 pages).
Kappos et al., "Oral Fingolimod (FTY720) for Relapsing Multiple Sclerosis", The New England Journal of Medicine, Sep. 14, 2006, pp. 1124-1140, vol. 355, No. 11, (17 pages).
Mehling et al., "FTY720 Therapy Exerts Differential Effects on T cell Subsets in Multiple Sclerosis", Neurology, Oct. 14, 2008, vol. 71, pp. 1261-1267 (eight (8) pages).
"Fingolimod", Pubchem, Aug. 8, 2005, pp. 1-3, Retrieved from https://pubchem.ncbi.nlm.nih.gov/compound/Flingolimod (three (3) pages).
Manouchehrinia et al., "Prevalence of a History of Prior Varicella/Herpes Zoster Infection in Multiple Sclerosis." Journal of Neurovirology, 2017, vol. 23, No. 83, 839-844, (six (6) pages).
Ross et al., "The Varicella Zoster Virus: A Pilot Trial of a Potential Therapeutic Agent in Multiple Sclerosis", J Clin Epidemiol, 1997, vol. 50, No. 1, pp. 63-68, (six (6) pages).

*Primary Examiner* — Raymond J Henley, III
(74) *Attorney, Agent, or Firm* — Crowell & Moring LLP

(57) ABSTRACT

The present application relates to a dosage regimen of an S1P receptor modulator or agonist in the course of the treatment of patients suffering from an inflammatory or autoimmune disease or disorder, for example multiple sclerosis (MS).

8 Claims, No Drawings

DOSAGE REGIMEN OF AN S1P RECEPTOR MODULATOR

FIELD OF THE PRESENT APPLICATION

The present application relates to a dosage regimen of an S1P receptor modulator or agonist in the course of the treatment of patients suffering from an inflammatory or autoimmune disease or disorder, for example multiple sclerosis (MS).

Multiple sclerosis is the chief cause of neurological disability in young adults and the most common demyelinating disorder of the central nervous system. Available therapies such as interferon-β and glatiramer acetate have modest efficacy and marginal effects on the progression of disability. These biological agents are administered parenterally and are associated, e.g., with injection site reactions and pyretic symptoms, such as flu-like symptoms. Therefore, there is a strong medical need for a safe and effective oral treatment of multiple sclerosis.

Of those people with multiple sclerosis who receive treatment, a significant number continue to experience disease activity clinically or experience side effects that include flu-like symptoms. Immediate post-injection reactions and injection site reactions. As a result, a substantial population of patients are untreated. Including many with active disease. These MS patients have either tried an existing therapy but discontinued due to intolerance, adverse effects, or perceived lack of efficacy or have not started any therapy because of their concern with adverse effects, fear of self-injection, fear of needles, or belief that currently available options are not effective enough to warrant trial. Thus, there is a significant unmet need for effective new therapies in MS, which limit or reduce the possible adverse events or side effects.

S1P receptor modulators are compounds which signal as agonists at one or more sphingosine1-phosphate receptors, e.g. S1P1 to S1P5. Agonist binding to a S1P receptor may e.g. result in dissociation of intracellular heterotrimeric G-proteins into Gα-GTP and Gβγ-GTP, and/or increased phosphorylation of the agonist-occupied receptor and activation of downstream signaling pathway kinases.

S1P receptor modulators are valuable compounds for the manufacture of medication for the treatment of various conditions in mammals, especially in human beings. For example, efficacy in transplantation has been demonstrated in rats (skin, heart, liver, small bowel), dogs (kidney), and monkeys (kidney) models. Due to their immune-modulating potency, S1P receptor modulators are also useful for the treatment of inflammatory and autoimmune diseases. Treating such diseases usually requires prolonged taking of medication, and maintaining the adequate drug regimen overtime.

Oral Fingolimod is the first compound in the new class of therapeutics called sphingosine 1-phosphate receptor modulators. Fingolimod is believed to reduce the number of lymphocytes circulating in the blood stream by reversibly trapping a proportion of them in the lymph nodes. Consequently, the number of activated lymphocytes reaching the brain is decreased, resulting in reduced inflammatory destruction. This is a new mechanism of action for MS.

Oral Siponimod is another compound in the new class of therapeutics called sphingosine 1-phosphate receptor modulators. Siponimod is believed to reduce the number of lymphocytes circulating in the blood stream by reversibly trapping a proportion of them in the lymph nodes. Consequently, the number of activated lymphocytes reaching the brain is decreased, resulting in reduced inflammatory destruction.

FTY720 efficacy in the treatment of multiple sclerosis has been shown in humans (e.g. as described in "FTY720 therapy exerts differential effects on T call subsets in multiple sclerosis". Mehling M, et al., Neurology. 2008 Oct. 14; 71(16):1281-7; and "Oral Fingolimod (FTY720) for relapsing multiple sclerosis". Kappos L, Antel J, Comi G, Montalban X, O'Connor P, Polman C H, Haas T, Kom A A, Karisson G, Radue E W; FTY720 D2201 Study Group. N Engl J Med. 2006 Sep. 14; 355(11):1124-40.).

Administration of a S1P receptor modulator, such as Fingolimod or Siponimod, may induce adverse events, such as a transient reduction of the heart rate and cardiac conduction at treatment initiation. In particular it has been described that administration of 1.25 mg of BAF-312 may induce a decrease in heart rate of approximately 8 beets/min ("FTY720: Placebo-Controlled Study of the Effect on Cardiac Rate and Rhythm in Healthy Patients", Robert Schmouder, Denise Serra, Yibin Wang, John M. Kovarik, John DiMarco, Thomas L. Hunt and Marie-Claude Bastien. J. Clin. Pharmacol. 2006; 46; 895.).

Because of such a possible adverse event, administration of the compound to the patients may have to be made under full and constant medical control, in order to check that the cardiac rhythm is maintained at an acceptable level and no high degree atrioventricular block occurs. Patients may have to stay in hospitals which complicate the treatment and increase the costs of treatment occurrence of adverse events during a drug treatment may induce patient hospitalization or prolongation of existing hospitalization.

Such possible events may also cause the patients to interrupt their treatment, change the recommended dosing regimen on their own or take the medication on an irregular basis, without any medical support or recommendation for doing that. While it is paramount for treating inflammatory or autoimmune diseases, such as for example multiple sclerosis, that the adequate medication is taken over a long period of time, sometimes during the whole life of the patient, and the adequate drug regimen is kept over such a long period of time.

Therefore, there is a need to reduce or manage the possible adverse events which may be generated by administration of such a S1P receptor modulator, while administering a dosage which is adequate to treat or prevent the disease for which the compound is administered during the required period of treatment.

More specifically, there is a need to provide an efficient treatment for treating an inflammatory or autoimmune disease or disorder, such as multiple sclerosis, for a large population of multiple sclerosis patients, including patients who could be more exposed or more sensitive to said possible adverse events, patients who were never treated or diagnosed for an inflammatory or autoimmune disease or disorder There is furthermore a need to ameliorate patient compliance.

BRIEF DISCLOSURE

Surprisingly it has been found that by administering a S1P receptor modulator or agonist, such as Siponimod, according to the specific dosage regimen or method of treatment of the present application, it is possible to treat the patient efficiently while controlling, reducing or abolishing the possible adverse events, e.g. side effects, which may be associated with administration of such a compound.

A further benefit is that the dosing regimen and methods of treatment of the present application permit to administer a S1P receptor modulator or agonist, such as Siponimod, to patients who otherwise may have been reluctant or not could not have been instructed to take that medication. In particular they permit to treat patients suffering from an inflammatory or autoimmune disease or disorder, such as multiple sclerosis, for which the ratio risk/benefit may otherwise be less favorable. Such patients are for example patients susceptible to or suffering from one or more disease or disorders affecting the heart or heart rhythm, respiratory functions, eyes, hepatic functions. This also concerns patients that have undergone an interruption or treatment holiday in the maintenance dosage regime e.g. a holiday of greater than 10 days.

Furthermore the dosing regimen and methods of treatment of the present application is applicable for patients who were already under treatment for an inflammatory or autoimmune or disease, for example under treatment for multiple sclerosis, as well as patients who were never treated or were not diagnosed for an inflammatory or autoimmune or disease before taking a S1P receptor modulator or agonist.

The dosage regimen of the present application is a regimen for a S1P receptor modulator or agonist therapy, which enables administration of a therapeutic dosage range of the S1P receptor to be achieved with controlled or minimal side effects, which could otherwise have been possibly associated with S1P receptor modulator therapy.

Another benefit of the present application is to provide an therapeutic regimen for an inflammatory or autoimmune or disease, such as multiple sclerosis, which can be personalized, e.g. adapted to the specific profile of the patient to be treated and/or to the state of the disease in this patient, in such a way that that the disease is treated (or the disease severity is reduced), while the adverse events which could otherwise have been associated with administering said S1P receptor modulator or agonist are controlled, reduced, or abolished. For example, therapeutic regimen of the present application may be personalized in view of the other diseases or disorders the patient could be affected with, the other medication he could be taken, e.g. depending on whether he is suffering from a heart disease or disorder.

In one embodiment, a method is provided for treating relapsing remitting multiple sclerosis in a patient in need thereof, the method comprising:

(a) identifying a patient suffering from relapsing remitting multiple sclerosis at risk of contracting infection caused by varicella zoster virus by testing said patient for a history of infection caused by varicella zoster virus, (b) vaccinating the patient at risk of contracting infection caused by varicella zoster virus, and (c) administering orally Siponimod or a pharmaceutically acceptable salt thereof to said patient at a daily dosage of 2 mg, thereby limiting the risk of infection caused by varicella zoster virus, wherein the relapsing remitting multiple sclerosis is treated by the administration of Siponimod. Treating may reduce the frequency of clinical exacerbations. The Siponimod may be administered as a hydrochloride salt. The infection may be chickenpox.

In another embodiment, a method is provided for treating multiple sclerosis in a patient in need thereof, the method comprising:

(a) identifying a patient suffering from multiple sclerosis at risk of contracting infection caused by varicella zoster virus by testing said patient for a history of infection caused by varicella zoster virus, (b) vaccinating the patient at risk of contracting infection caused by varicella zoster virus, and (c) administering orally a therapeutically effective amount of Siponimod or a pharmaceutically acceptable salt thereof to said patient, thereby limiting the risk of infection caused by varicella zoster virus, wherein the multiple sclerosis is treated by the administration of Siponimod. The multiple sclerosis may be primary progressive multiple sclerosis. The Siponimod may be administered in a dosage of 0.25 mg twice per day or a dosage of 2 mg per day.

DETAILED DISCLOSURE

S1P Receptor Modulators or Agonists

The present application encompasses S1P receptor modulators, agonists, and antagonists. In some embodiments, the S1P receptor modulators, agonists, and antagonists are compounds as described in U.S. Pat. Nos. 7,939,519 and 8,492,441.

In a preferred embodiment of the present application, the S1P receptor modulator is Siponimod. In the present application, Siponimod may be referred to as by its IUPAC name, which is: 1-({4-[(1E)-1-({[4-Cyclohexyl-3-(trifluoromethyl) phenyl]methoxy}imino)ethyl]-2-ethylphenyl}methyl)azetidine-3-carboxylic acid.

In the present application, Siponimod may also be referred to by its trade name, MAYZENT. In the present application, Siponimod may also be referred to by the designation BAF-312.

In the present application, Siponimod may also be referred to by chemical structure, shown below:

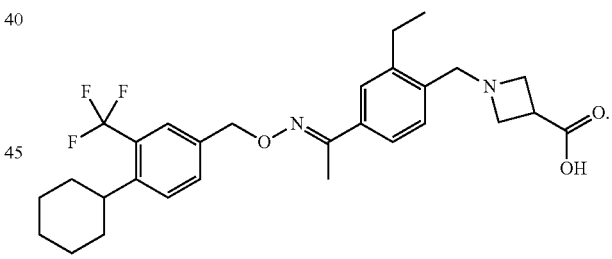

It will be understood by a person of ordinary skill in the art that such designations of Siponimod are interchangeable, and each designation refers to the same compound.

Other preferred embodiments of the present application include pharmaceutically acceptable salts, prodrugs, or stereoisomers of Siponimod.

Another specific S1P receptor modulator of the present application is the phosphorylated derivative of Siponimod, also referred to as Siponimod-phosphate.

Preferably, the S1P receptor modulator or agonist of the present application, e.g. Siponimod in free form, in a pharmaceutically acceptable salt form or Siponimod-phosphate, is administered orally.

Dosage Regimen

As previously stated, the present application provides a new dosage regimen and method for treating an inflammatory or autoimmune disease or disorder in a patient in need thereof, comprising administering to said patient a S1P receptor modulator or agonist, such as Siponimod (BAF-312), a phosphate derivative thereof or a pharmaceutically acceptable salt thereof, in such a way that the disease is treated or the disease severity is reduced, while the adverse events possibly associated with administration of said S1P receptor modulator or agonist are controlled, limited, reduced or abolished. For example there is provided a method for treating an inflammatory or autoimmune disease or disorder in a patient in need thereof, comprising administering to said patient a S1P receptor modulator or agonist, such Siponimod (BAF-312), a phosphate derivative thereof or a pharmaceutically acceptable salt thereof, in such a way that the symptoms of the disease are reduced or abolished while the adverse events possibly associated with administration of said S1P receptor modulator or agonist are controlled, limited, reduced or abolished.

According to the present application there is provided a method for administering BAF-312, a phosphate derivative thereof or a pharmaceutically acceptable salt thereof, to a patient in need thereof preferably refers to a method for treating an inflammatory or autoimmune disease or disorder, limiting the symptoms associated thereof or the progression thereof, e.g. multiple sclerosis, in a patient in need thereof. In particular it refers to a method for treating RRMS, limiting the symptoms associated thereof or the progression thereof in a patient in need thereof.

According to the present application the terms "treatment" or "treat" refer to both prophylactic or preventive treatment as well as curative or disease-modifying treatment, including treatment of patients at risk of contracting the disease or disorder, or suspected to have contracted the disease or disorder, as well as patients who are ill or have been diagnosed as suffering from the disease or disorder.

Autoimmune diseases or disorders according to the present application are preferably chronic long-term diseases, e.g. multiple sclerosis (MS), for example relapsing remitting multiple sclerosis (RRMS) or primary progressive multiple sclerosis (PPMS), e.g. RRMS. MS takes several forms, with new symptoms occurring either in discrete attacks (relapsing forms) or slowly accumulating over time (progressive forms).

The dosing regimens and methods of treatment according to the present application are particularly adapted for multiple sclerosis, e.g. RRMS.

As herein defined, treating multiple sclerosis refers to, but is not limited to, reducing the frequency of clinical exacerbations or delaying the accumulation of physical disability induced by multiple sclerosis. It may also refer to limiting the symptoms of the disease.

As herein defined, symptoms or disorders associated with multiple sclerosis encompass neurological symptoms, physical and cognitive disability and neuropsychiatric disorders.

As herein defined, adverse event refers to any adverse change in health that occurs to a patient receiving a treatment or within a specified period of time after the treatment has been completed. Controlling the adverse events refers to limiting the extension, outcome, consequences or impact of such events in such a way that the patient's health is not a risk, or the treatment can be continued without worsening the overall health of the patient. The adverse events are not necessarily related to the medication itself; they may also be related to the inflammatory or autoimmune disease or disorder for which the patient is treated or another disease or disorder that the patient is further affected with.

According to the present application, reduction of the adverse events refers to the reduction of the events, e.g. of side-effects, to a level that is acceptable to the patient safety, e.g. which does not require specific treatment and/or specific medical care, hospitalization or medical monitoring. For example, reduction of the adverse events refers to the reduction of the events to a level that is acceptable for the patient compliance.

According to the present application, limitation of the adverse events refers to limitation of the number or occurrence of adverse events, e.g. of side-effects, in a patient, to a number or occurrence which is acceptable to the patient, e.g. which does not require specific treatment and/or specific medical care, hospitalization or medical monitoring. For example, limitation of the adverse events refers to limitation of the number or occurrence of adverse events to a number or occurrence that is acceptable for the patient safety end/or compliance.

The monitoring of possible adverse events may be done as described herein above. For example, it may be done by ophthalmic examination, dermatologic examination, pulmonary function tests, chest X-ray and/or CT, Holter monitoring, and/or echocardiography. In a specific embodiment of the present application, the monitoring and reporting of adverse events comprises the monitoring and reporting of bradycardia, syncope or pre-syncope, serious infectious, liver toxicity, and macular edema.

As herein defined, a patient treated with Siponimod (BAF-312) refers to a patient receiving Siponimod (BAF-312), a phosphate derivative thereof (i.e. Siponimod-phosphate) or a pharmaceutically acceptable salt thereof, for treating an inflammatory or autoimmune disease or disorder according to the present application, e.g. MS, e.g. RRMS.

As herein defined, a patient in need of prescribing Siponimod refers to a patient suffering from an inflammatory or autoimmune disease or disorder according to the present application, e.g. a MS patient.

Patients treated with Siponimod (BAF-312) and the patients in need of prescribing Siponimod may be patients who have never received treatment for an inflammatory or autoimmune disease or disorder, such as patients who have never received a treatment for treating or preventing MS, as well as patients who previously received one or more treatment for an inflammatory or autoimmune disease or disorder, for example who previously received one or more treatment for MS.

The effectiveness of the S1P modulator of the present application in treating multiple sclerosis may be evaluated by medical standards and criteria known to the skilled person. For example, it can be evaluated through annual relapse rate of multiple sclerosis.

For example, the dosage of the S1P receptor modulator or agonist of the present application can be considered as efficient for treating the disease or reducing the symptoms associated thereof, e.g. for treating multiple sclerosis, when the relapse rate is decreased by more than 45%, e.g. more than 50%, e.g. more than 80%.

In another embodiment effectiveness of the S1P receptor modulator or agonist of the present application in treating multiple sclerosis is evaluated through the disability progression, e.g. according to the Kurtzke Expanded Disability Status Scale (EDSS). The Kurtzke Expanded Disability Status Scale (EDSS) is a method of quantifying disability in multiple sclerosis. The EDSS quantifies disability in eight Functional Systems (FS) and allows neurologists to assign a Functional System Score (FSS) in each of these. For example, the dosage of the S1P receptor modulator or agonist of the present application can be considered as efficient for treating the disease or reducing the symptoms associated thereof, e.g. for treating multiple sclerosis, when progression of the patient disability is delayed by at least 25%, e.g. by at least 30%, e.g. by at least 32%.

The effectiveness of the dosing regimen of the present application may also be evaluated by measuring brain lesions. e.g. by Magnetic Resonance Imaging (RMI) scans. Monitoring The present application provides a dosing regimen and a method for treating an inflammatory or autoimmune disease or disorder in a patient in need thereof, comprising administering to said patient a therapeutically effective amount of a S1P receptor modulator or agonist, wherein said method comprises the steps of
  i) monitoring the patient during a specific period of time after the first administration of said S1P receptor modulator or agonist, and
  ii) optionally interrupting the administration of said S1P receptor modulator or agonist and/or modifying the treatment regimen thereof and/or administering a second drug which mitigates said possible adverse events.

Such a dosing regimen is particularly adapted for administering Siponimod, e.g. in a patient suffering from multiple sclerosis.

Furthermore, there is provided a S1P receptor modulator or agonist, e.g. BAF-312, a phosphate derivative thereof or a pharmaceutically acceptable salt thereof, for use in the treatment of an inflammatory or an autoimmune disease or disorder, e.g. multiple sclerosis, wherein said treatment comprises the steps of
  i) monitoring the patient during a specific period of time after the first administration of said S1P receptor modulator or agonist, and
  i) optionally interrupting the administration of said S1P receptor modulator or agonist and/or modifying the treatment regimen thereof and/or administering a second drug which mitigates said possible adverse events.

In a specific embodiment, the present application provides BAF-312, a phosphate derivative thereof or a pharmaceutically acceptable salt thereof, e.g. the hydrochloride salt of BAF-312, for use in the treatment of multiple sclerosis, wherein said treatment comprises the steps of
  i) monitoring the patient during a specific period of time after the first administration of BAF-312, a phosphate derivative thereof or a pharmaceutically acceptable salt thereof, and
  i) optionally interrupting the administration of BAF-312, a phosphate derivative thereof or a pharmaceutically acceptable salt thereof, and/or modifying the treatment regimen thereof, and/or administering a second drug which mitigates said possible adverse events.

The present application further pertains to a S1P receptor modulator or agonist, e.g. BAF-312, a phosphate derivative thereof or a pharmaceutically acceptable salt thereof, for use in a method for treating an inflammatory or an autoimmune disease or disorder, e.g. multiple sclerosis, wherein said method comprises the steps of
  i) monitoring the patient during a specific period of time after the first administration of said S1P receptor modulator or agonist, and
  N) optionally interrupting the administration of said S1P receptor modulator or agonist and/or modifying the treatment regimen thereof and/or administering a second drug which mitigates said possible adverse events.

In a specific embodiment, the present application pertains to BAF-312, a phosphate derivative thereof or a pharmaceutically acceptable salt thereof for use in a method for the treatment of multiple sclerosis, wherein said treatment comprises the steps of
  i) monitoring the patient during a specific period of time after the first administration of said S1P receptor modulator or agonist, and
  i) optionally interrupting the administration of said S1P receptor modulator or agonist and/or modifying the treatment regimen thereof and/or administering a second drug which mitigates said possible adverse events.

According to the present application, the action taken on step ii) depends on the results obtained under step i).

When the S1P receptor modulator or agonist is selected from Siponimod (BAF-312), a phosphate derivative thereof or a pharmaceutically acceptable salt thereof, the step of modifying the treatment regimen may consist of administering a daily dosage of the drug that is lower than about 2 mg and then increasing the dosage up to a daily dosage of about 2 mg. The daily dosage of the drug may then be increased stepwise, e.g. by titration. It may also consist of administering a daily dosage of the drug higher than 2 mg, e.g. a daily dosage of about 3 mg or about 4 mg or about 5 mg or about 6 mg.

In a specific embodiment of the present application, e.g. when the S1P receptor modulator or agonist is selected from Siponimod (BAF-312), a phosphate derivative thereof or a pharmaceutically acceptable salt thereof, the step of modifying the treatment regimen may consist of increasing the period of time between two consecutive administrations of the medication.

According to the present application, there is provided a patient monitoring, i.e. a specific monitoring of patients treated with a S1P receptor modulator or agonist, such as Siponimod (BAF-312), a phosphate derivative thereof or a pharmaceutically acceptable salt thereof, in order to control, limit or abolish the possible adverse events, wherein said monitoring is performed before and/or during administration of the medication.

The patient monitoring of the present application comprises
  a) monitoring infections or infestations, e.g. viral infections, throughout administering said S1P receptor modulator or agonist, and/or
  b) performing an ophthalmologic examination.

The patient monitoring may further comprise one or more steps of
  c) monitoring the heart rate of the patient at least during the first hours after the first administration of said S1P receptor modulator or agonist,
  d) observing the patient during the first hours after the first administration of said S1P receptor modulator or agonist, to monitor the heart rate of the patient,
  e) performing liver function tests,
  f) performing dermatological examinations,
  g) performing pulmonary functions tests.

The patient monitoring may further comprise one or more steps of
  h) determining complete blood counting (CBC),
  i) lymphocytes counting and/or recording of blood key parameters,
  j) monitoring and/or recording of vital signs, e.g. heart rate, blood pressure, e.g. arterial blood pressure.
  k) monitoring and/or recording of cardiac disorders,
  l) monitoring and/or recording of other adverse events or side-effects.

The present application also provides a dosing regimen and a method of controlling, reducing, or abolishing the possible adverse events associated with treating a patient suffering from an inflammatory or autoimmune disease or disorder with a S1P receptor modulator or agonist, comprising administering to said patient a therapeutically effective amount of said S1P receptor modulator or agonist, wherein said method comprises i) a patient monitoring as defined herein above, and
  ii) optionally interrupting the administration of said S1P receptor modulator or agonist and/or modifying the treatment regimen thereof.

In one embodiment of the present application, the patient monitoring of the present application may comprise one or more of the following steps, optionally all the steps of,
  complete blood counting (CBC),
  lymphocytes counting,
  analysis of liver enzymes,
  monitoring and/or recording of vital signs, e.g. heart rate, blood pressure, e.g. arterial blood pressure,
  testing history of viral infection or viral serology, e.g. regarding chickenpox.
  monitoring and/or recording of infections or infestations, e.g. viral infections,
  dermatological examinations,
  ophthalmologic examinations,
  examinations of pulmonary function,
  monitoring and/or recording of cardiac disorders,
  monitoring and/or recording of blood key parameters,
  monitoring and/or recording of liver function tests,
  monitoring and/or recording of other adverse events or side-effects.

Preferably, the patient monitoring of the present application comprises one or more of the following steps, optionally all the steps of:
  complete blood counting (CBC),
  analysis of liver enzymes,
  ophthalmologic examinations, and
  testing history of viral infection or viral serology, e.g. regarding chickenpox,
  monitoring and/or recording of infections or infestations, e.g. viral infection.

The patient monitoring of the present application may further comprise
  establishing an electrocardiogram (ECG), e.g. at starting administration with the medication, and/or
  vaccinate the patient before starting administration, e.g. against varicella zoster virus (VZV).

As herein defined, the patient monitoring of the present application may comprise or more of the above described monitoring steps.

In one embodiment of the present application, the patient monitoring comprises the steps of
  monitoring and/or recording of infections or infestations, e.g. viral infections,
  performing ophthalmologic examinations, and optionally further comprises the steps of
  monitoring and/or recording of cardiac disorders for specific category of patients, and/or
  performing dermatological examinations.

In another embodiment of the present application, the patient monitoring comprises the steps of
  monitoring end/or recording of infections or infestations, e.g. viral infections,
  ophthalmologic examinations.
  monitoring and/or recording of cardiac disorders. e.g. for specific category of patients,
  liver function tests;
  and optionally further comprises the steps of
  dermatological examinations.

In yet a further embodiment of the present application, the patient monitoring comprises the steps of
  monitoring the heart rate of the patient,
  monitoring and/or recording of infections or infestations, e.g. viral infections,
  performing ophthalmologic examinations,
  and optionally further comprises the steps of
  performing dermatological examinations.

In yet another embodiment of the present application, the patient monitoring comprises the steps of
  monitoring and/or recording of infections or infestations, e.g. viral infections,
  performing an ophthalmologic examination within the first 1 to 10 after starting administration,
  observing patients for at least 6 hours after the first dose administration, and optionally further comprises the steps of
  dermatological examinations.

The patient monitoring may further comprise a step of monitoring and/or recording of liver function tests in case patients develop symptoms suggestive of hepatic dysfunction.

In a preferred embodiment of the present application, there is provided a method of prescribing Siponimod (BAF-312), a phosphate derivative thereof or a pharmaceutically acceptable salt thereof, to a patient in need thereof, in such a way as to limit the possible adverse events before or during administration of Siponimod, wherein said method comprises the patient monitoring as herein above described.

For example, the method of prescribing Siponimod may comprise one or more of the following steps:
  performing lymphocyte counting,
  monitoring and/or recording of vital signs, e.g. blood pressure, e.g. arterial blood pressure,
  monitoring and/or recording of infections or infestations, e.g. viral infections,
  performing dermatological examinations,
  performing ophthalmologic examinations,
  performing examinations of pulmonary function,
  monitoring and/or recording of cardiac disorders,
  monitoring and/or recording of blood key parameters, e.g. level of serum ALT,
  performing liver function tests,
  monitoring and/or recording of other adverse events or side-effects, and
  wherein each of said steps is performed for a specific period of time before and/or during the period of administering the drug.

The specific and regular monitoring of the treated patients may consist of one or more of the following steps
  performing lymphocyte counting,
  monitoring and/or recording of vital signs, e.g. blood pressure, e.g. arterial blood pressure,
  monitoring and/or recording of infections or infestations, e.g. viral infections,
  performing dermatological examinations,
  performing ophthalmologic examinations,
  performing examinations of pulmonary function,
  monitoring and/or recording of cardiac disorders,
  monitoring and/or recording of blood key parameters, e.g. level of serum ALT,
  performing liver function tests,
  monitoring and/or recording of other adverse events or side-effects, and wherein said steps are performed for a specific period of time before and/or during the period of administering the drug.

Each step may be performed as further explained below.

Preferably, the patient monitoring may consist of one or more of the following steps:
monitoring and/or recording of infections or infestations, e.g. viral infections, during FTY720 therapy,
ophthalmologic examinations as herein defined,
monitoring and/or recording of cardiac disorders for specific category of patients,
liver function tests in case patients develop symptoms suggestive of hepatic dysfunction,
and optionally further comprises the steps of
dermatological examinations.

The different steps the patient monitoring of the present application are performed at a specific period of time after administration of the first dose.

These steps can be performed as described herein.

In a specific embodiment of the present application, the treated patients are monitored under supervision of medical doctors for a specific period of time after the first dose administration, for the first 1 to 10 hours after the first administration of the S1P receptor modulator or agonist, e.g. Siponimod, a phosphate derivative thereof or a pharmaceutically acceptable salt thereof, for at least 6 hours after the first dose administration.

According to the present application, one or more of these steps, e.g. monitoring and/or recording of cardiac disorders, are performed at least 4 hours after the first dose administration, e.g. at least for 6 hours after the first dose administration, or at least 8 hours alter the first dose administration, e.g. 3 to 8 hours after the first dose administration, e.g. 4 to 6 hours after the first dose administration, e.g. 4 to 6 hours after the first dose administration. Preferably monitoring and/or recording of cardiac disorders are performed about 6 hours after the first dose administration The step of monitoring and/or recording of cardiac disorders may consist of observing patients during that period of time after the first dose administration, e.g. during at least 4 hours after the first dose administration, e.g. at least for 6 hours after the first dose administration, or at least 8 hours after the first dose administration.

According to the present application, the cardiac disorders which are monitored and/or recorded comprise but are not limited to bradycardia and high-grade AV block.

According to the present application, the infections which are recorded or monitored are for example viral infections, e.g. varicella zoster virus (VZV), influenza viral infection, herpes viral infection, lower respiratory tract infection, e.g. bronchitis and pneumonia.

In an embodiment of the present application, the monitoring of infections or infestations is performed within the first three months after the first dose administration, e.g. within the first two months after the first dose administration. In another embodiment of the present application, the monitoring of infections or infestations is performed throughout administration of the medication.

Prior to starting to administer the S1P receptor modulator or agonist, the patient may be tested for history of infections, e.g. viral infection, in particular chickenpox. In case the searched serology is negative, the patient may be vaccinated, e.g. against varicella zoster virus or influenza virus.

The monitoring or recording of infections or infestations, e.g. viral infections, may be performed with medical techniques available, for example through complete blood counting (CBC) and/or lymphocytes counting.

According to the present application, the ophthalmologic examination preferably comprises the checking and/or monitoring of disturbances in visual acuity, e.g. appearance of macular edema.

In a specific embodiment of the present application, eye examinations include at least one of eye history, visual acuity, dilated ophthalmoscopy, Optical Coherence Tomography (OCT), evaluation of the fundus. Such examinations are preferably performed by an ophthalmologist.

According to the present application, ophthalmologic examination may be performed after initiating the administration with S1P receptor modulator or agonist, e.g. after commencing BAF-312 therapy, e.g. within the first 1 to 12 months, e.g. 2 to 10 months, e.g. 2 to 6 months, e.g. 2 to 5 months, e.g. 3 to 4 months. Additional ophthalmologic examinations may be performed as needed based on patient symptoms, e.g. at intervals determined by the ophthalmologist.

According to the present application, the ophthalmologic examination may comprising the steps of
1) identifying the eye diseases history of the patient to be treated before commencing the treatment with BAF-312,
2) having ophthalmologic examinations performed as herein above mentioned, e.g. 3 to 4 months after commencing the treatment with BAF-312, preferably by an ophthalmologist, and optionally
3) having additional ophthalmologic examinations performed based on patient symptoms, e.g. at intervals determined by the ophthalmologist.

Ophthalmologic examination may also be performed before starting the administration with S1P receptor modulator or agonist, e.g. before starting BAF-312 therapy. This embodiment is particularly adapted for specific patients' categories, for example in case of patients who have an eyes disease or disorder, and/or history of diabetes or uveitis.

According to the present application, the dermatological examination may comprise the checking of appearance e.g. of neoplasms, skin malignancies, melanoma, squamous cell carcinoma, basal cell carcinoma. Dermatological screening may be performed prior to, or shortly after initiation of therapy. In a specific embodiment of the present application, dermatological screenings are performed annually in patient receiving the S1P receptor modulator or agonist, e.g. BAF-312, a phosphate derivative thereof or a pharmaceutically acceptable salt thereof.

Dermatological screening may be performed by a physician, e.g. a dermatologist. In another embodiments, such screening is performed more frequently, e.g. by the patient himself.

According to the present application, the examinations of pulmonary function may be performed by spirometry, pulmonary function tests, e.g. FEV1, FVC, FEF25-75%, DLCO, diffusion capacity for carbon monoxide, or chest high resolution computed tomography (HRCT).

In a specific embodiment of the present application the pulmonary function test (PFT) is performed a few hours to a few days after the first administration, for example at the day of the first administration, for example from 2 to 12 hours after the first drug administration, for example from 2 to 8 hours after the first drug administration, for example from 2 to 6 hours after the first administration, for example at 6-hour after the first administration. A second PFT may be performed a few days after the first administration, for example from 2 to 10 days after the first drug administration, for example from 3 to 8 days first drug administration, for example about a week after the first drug administration.

In a specific embodiment of the present application the level of liver enzyme, e.g. serum ALT, is evaluated at initiation of therapy and optionally periodically thereafter. Continuous evaluation is particularly adapted in case of patients who develop symptoms suggestive of hepatic dysfunction.

According to the present application, the liver function tests may be performed for specific category of patients, e.g. patients who develop symptoms suggestive of hepatic dysfunction, e.g. nausea, vomiting, abdominal pain, anorexia, or jaundice.

According to the present application, monitoring and/or recording of liver function tests may comprise any one of the steps of 1) identifying the level of liver enzyme, e.g. serum ALT, in the patient to be treated before the first administration of the S1P receptor modulator or agonist, e.g. BAF-312, a phosphate derivative thereof or a pharmaceutically acceptable salt thereof, and administering the first dose only if alanine aminotransferase (ALT) level is not more than 2 times the upper limit of the normal range (ULN),
2) identifying the level of liver enzyme, e.g. serum ALT, in the patient under therapy, and discontinue the therapy in patients experiencing jaundice or elevation of liver enzyme is more than 5 times the upper limit of the normal range (ULN).

The patient monitoring of the present application may comprise a step of observing the patient for the first 1 to 10 hours after the first administration of the S1P receptor modulator or agonist, e.g. Siponimod, a phosphate derivative thereof or a pharmaceutically acceptable salt thereof, e.g. the first 2 to 8 hours after the first administration, e.g. the first 3 to 9 hours after the first administration, e.g. the first 2 to 8 hours after the first administration, e.g. the first 4 to 7 hours after the first administration, e.g. the first 6 hours, e.g. the first 5 hours, e.g. the first 4 hours after the first administration of said S1P receptor modulator or agonist, e.g. Siponimod, a phosphate derivative thereof or a pharmaceutically acceptable salt thereof. For example, the patient monitoring of the present application may comprise a step of observing the patient at least 2 hours after the first administration of said S1P receptor modulator or agonist, e.g. Siponimod, a phosphate derivative thereof or a pharmaceutically acceptable salt thereof. e.g. at least 4 hours after the first administration, e.g. at least 6 hours after the first administration.

According to the present application, there is provided a method for treating an inflammatory or autoimmune disease or disorder in a patient in need thereof, comprising administering to said patient a therapeutically effective amount of S1P receptor modulator or agonist, wherein specific parameters of the patient are checked before initiating said treatment, and if necessary, the treatment regimen is adapted and/or a second drug which mitigates the adverse events which could possibly occur.

The present application further pertains to a S1P receptor modulator or agonist, e.g. BAF-312, a phosphate derivative thereof or a pharmaceutically acceptable salt thereof, for use in a method of treating an inflammatory or an autoimmune disease or disorder, e.g. multiple sclerosis, wherein said method comprises the steps of checking specific parameters of the patient before initiating said treatment, and if necessary adapting the treatment regimen thereof and/or administering a second drug which mitigates the adverse events which could possibly occur.

Said parameters are selected from signs of infections or infestations (e.g. viral infections), visual acuity, presence of eye disease, liver enzymes, blood pressure, blood analysis (e.g. complete blood count), electrocardiogram (ECG), pulmonary function, presence of skin disease or disorder, and liver function.

In a specific embodiment, these parameters are selected from signs of infections or infestations (e.g. viral infections), visual acuity, liver enzymes and blood pressure, and optionally heart rate.

For example, an ECG is performed before initiating administration with said S1P receptor modulator or agonist.

These parameters may also be checked throughout the treatment with said S1P receptor modulator or agonist.

In a specific embodiment of the present application there is provided

1—a method for administering a S1P receptor modulator or agonist, e.g. Siponimod, a phosphate derivative thereof or a pharmaceutically acceptable salt thereof, in a patient in need thereof, comprising the steps of
a.) identifying the eye diseases history of the patient to be treated before commencing the treatment with said S1P receptor modulator or agonist,
b.) having ophthalmologic examinations performed as herein above mentioned, e.g. 3 to 4 months after commencing the treatment with said S1P receptor modulator or agonist, preferably by an ophthalmologist, and optionally
c.) having additional ophthalmologic examinations performed based on patient symptoms, e.g. at intervals determined by the ophthalmologist.

2—A method for treating an inflammatory or autoimmune disease or disorder (for example multiple sclerosis), and limiting the symptoms associated thereof or reducing the severity of the disease, in a patient in need thereof, comprising the steps a.), b.) and c.) as defined above.

3—a S1P receptor modulator or agonist, e.g. BAF-312, a phosphate derivative thereof or a pharmaceutically acceptable salt thereof, for use in a method for treating an inflammatory or an autoimmune disease or disorder, e.g. multiple sclerosis, wherein said method comprises the steps a.), b.) and c.) as defined above.

4—a S1P receptor modulator or agonist, e.g. BAF-312, a phosphate derivative thereof or a pharmaceutically acceptable salt thereof, for use in the treatment of an inflammatory or an autoimmune disease or disorder, e.g. multiple sclerosis, wherein said treatment comprises the steps a.), b.) and c.) as defined above.

5—BAF-312, a phosphate derivative thereof or a pharmaceutically acceptable salt thereof, e.g. the hydrochloride salt of BAF-312, for use in a method for the treatment of multiple sclerosis, wherein said treatment comprises the steps of
a') identifying the eye diseases history of the patient to be treated before commencing the treatment with BAF-312, phosphate derivative or pharmaceutically acceptable salt thereof,
a.) having ophthalmologic examinations performed as herein above mentioned, e.g. 3 to 4 months after commencing the treatment with BAF-312, phosphate derivative or pharmaceutically acceptable salt thereof, preferably by an ophthalmologist, and optionally
b.) having additional ophthalmologic examinations performed based on patient symptoms, e.g. at intervals determined by the ophthalmologist.

6—BAF-312, a phosphate derivative thereof or a pharmaceutically acceptable salt thereof, e.g. the hydrochloride salt of BAF-312, for use in the treatment of multiple sclerosis, wherein said treatment comprises the steps a'.), b'.) and c'.) as defined above.

In a specific embodiment of the present application there is provided

7—A method for administering a S1P receptor modulator or agonist, e.g. Siponimod, a phosphate derivative thereof or a pharmaceutically acceptable salt thereof, in a patient in need thereof, comprising the steps of d) identifying the level of liver enzyme, e.g. serum ALT, in the patient to be treated before the first administration of said S1P receptor modulator or agonist, and administering the first dose only if ALT level is not >2√6ULN, and e) identifying the level of liver enzyme, e.g. serum ALT, in the patient under therapy, and discontinue the therapy in patients experiencing jaundice or elevation of liver enzyme >5√6ULN.

8—A method for treating an inflammatory or autoimmune disease or disorder (for example multiple sclerosis), and limiting the symptoms associated thereof or reducing the severity of the disease, in a patient in need thereof, comprising the steps d.), and e.) as defined above.

9—A S1P receptor modulator or agonist, e.g. BAF-312, a phosphate derivative thereof or a pharmaceutically acceptable salt thereof, for use in a method for treating an inflammatory or an autoimmune disease or disorder, e.g. multiple sclerosis, wherein said method comprises the steps d.), and e.) as defined above.

10—A S1P receptor modulator or agonist, e.g. BAF-312, a phosphate derivative thereof or a pharmaceutically acceptable salt thereof, for use in the treatment of an inflammatory or an autoimmune disease or disorder, e.g. multiple sclerosis, wherein said treatment comprises the steps d.), and e.) as defined above.

11—BAF-312, a phosphate derivative thereof or a pharmaceutically acceptable salt thereof, e.g. the hydrochloride salt of BAF-312, for use in a method for the treatment of multiple sclerosis, wherein said method comprises the steps of d') identifying the level of liver enzyme, e.g. serum ALT, in the patient to be treated before the first administration of BAF-312, a phosphate derivative thereof or a pharmaceutically acceptable salt thereof, and administering the first dose only if ALT level is not >2×ULN, and e') identifying the level of liver enzyme, e.g. serum ALT, in the patient under therapy, and discontinue the therapy in patients experiencing jaundice or elevation of liver enzyme >5×ULN 12—BAF-312, a phosphate derivative thereof or a pharmaceutically acceptable salt thereof, e.g. the hydrochloride salt of BAF-312, for use in the treatment of multiple sclerosis, wherein said treatment comprises the steps d'.), and e'.) as defined above.

In yet another embodiment of the present application there is provided

13—A method for administering a S1P receptor modulator or agonist, e.g. BAF-312, a phosphate derivative thereof or a pharmaceutically acceptable salt thereof, in a patient in need thereof and receiving concomitant beta-blocker therapy, comprising the steps of f) measuring heart rate and/or blood pressure of the patient to be treated before commencing the treatment with said S1P receptor modulator or agonist, g) either measuring heart rate every 3 to 5 hour, e.g. every four hour, for at least 6-hour hereafter, and/or perform an ECG 3 to 6 hours, e.g. 4 to 6 hours, post-dose, and h) administering an adequate treatment if bradyarrhythmia-related symptom is seen under step g), e.g. atropine or isoprenaline.

In one embodiment, that method refers to a method for administering BAF-312, a phosphate derivative thereof or a pharmaceutically acceptable salt thereof, e.g. the hydrochloride salt of BAF-312, in a patient affected by multiple sclerosis.

14—A method for treating an inflammatory or autoimmune disease or disorder (for example multiple sclerosis), and limiting the symptoms associated thereof or reducing the severity of the disease, in a patient in need thereof, comprising the steps f.), g.) and h.) as defined above.

15—A S1P receptor modulator or agonist, e.g. BAF-312, a phosphate derivative thereof or a pharmaceutically acceptable salt thereof, for use in a method for treating an inflammatory or an autoimmune disease or disorder, e.g. multiple sclerosis, wherein said method comprises the steps f.), g.) and h.) as defined above.

16—A S1P receptor modulator or agonist, e.g. BAF-312, a phosphate derivative thereof or a pharmaceutically acceptable salt thereof, for use in the treatment of an inflammatory or an autoimmune disease or disorder, e.g. multiple sclerosis, wherein said treatment comprises the steps f.), g.) and h.) as defined above.

17—BAF-312, a phosphate derivative thereof or a pharmaceutically acceptable salt thereof, e.g. the hydrochloride salt of BAF-312, for use in a method for the treatment of multiple sclerosis, wherein said method comprises the steps of f') measuring heart rate and/or blood pressure of the patient to be treated before commencing the treatment with BAF-312, a phosphate derivative thereof or a pharmaceutically acceptable salt thereof, g') either measuring heart rate every 3 to 5 hour, e.g. every four hour, for at least 6-hour hereafter, and/or perform an ECG 3 to 6 hours, e.g. 4 to 8 hours, post-dose, and h') administering an adequate treatment if bradyarrhythmia-related symptom is seen under step g), e.g. atropine or isoprenaline.

18—BAF-312, a phosphate derivative thereof or a pharmaceutically acceptable salt thereof, e.g. the hydrochloride salt of BAF-312, for use in the treatment of multiple sclerosis, wherein said treatment comprises the steps of f.), g'.) and h'.) as defined above.

In yet another embodiment of the present application there is provided

19—A method for administering a S1P receptor modulator or agonist, e.g. BAF-312, a phosphate derivative thereof or a pharmaceutically acceptable salt thereof, in a patient in need thereof, comprising the steps of i) observing the patient after the first dose administration for an observing period as defined hereinabove, e.g. for at least 6 hours j) measuring heart rate of the patient after this period, k) either releasing the patient if the if the is >40 bpm, or of 40-60 bpm e.g. in case this value is not the lowest heart rate measured during the 6-hour observation period; or maintaining the patient in an appropriate setting.

Such a method is particularly adapted to patients with low resting heart rate (e.g. lower than 50) or those taking beta blockers, or having high grade atrioventricular (AV) block or sick-sinus syndrome.

In a specific embodiment, that method refers to a method for administering BAF-312, a phosphate derivative thereof or a pharmaceutically acceptable salt thereof, e.g. the hydrochloride salt of BAF-312, in a patient affected by multiple sclerosis.

The present application also provides
20—BAF-312, a phosphate derivative thereof or a pharmaceutically acceptable salt thereof, e.g. the hydrochloride salt of BAF-312, for use in the treatment of multiple sclerosis, wherein said treatment comprises the steps i.), j.) and k.) as defined above.
21—BAF-312, a phosphate derivative thereof or a pharmaceutically acceptable salt thereof, e.g. the hydrochloride salt of BAF-312, for use in a method of treating multiple sclerosis, wherein said method comprises the steps i.), j.) and k.) as defined above.

In specific cases, e.g. when patients experiencing symptomatic events associated with bradyarrhythmia not resolved by the end of the 6-hour observation, day 2 dose may also be performed with an observation period like the first administration, e.g. as described above.

An observation period as defined hereinabove, e.g. 6 hour observation, may also be performed in case of a patient restarting the S1P receptor modulator or agonist, e.g. BAF-312, a phosphate derivative thereof or a pharmaceutically acceptable salt thereof, after a drug interruption of more than 4 days, e.g. more than 6 days, e.g. more than 8 days, e.g. more than 10 days, e.g. more than 12 days, e.g. more than 14 days, e.g. more than 18 days, e.g. more than 21 days.

In another embodiment of the present application, there is provided a method for administering BAF-312, a phosphate derivative thereof or a pharmaceutically acceptable salt thereof, to a patient in need thereof while controlling, limiting or abolishing the possible adverse events associated or in relation to such an administering, wherein the patients at possible risk of showing such events are identified before administering the drug and specific and regular monitoring of the treated patients is performed, e.g. by an adequate physician.

The patients at possibly increased risk may be patients selected from patients who have eyes diseases or disorders; patients who show a high ALT level, patients who have hepatic dysfunction, patients who have hypertension; and patients who have heart failure or arrythmias. It may also concern patient affected by asthma, for example moderate asthma and/or diabetic patients.

In another embodiment, it can be pregnant women.

As herein defined, an eyes disease or disorder refers to a disease or disorder impacting eyes, e.g. uveitis, diabetes.

Patients who show a high ALT level refers to patients who show an ALT level of, or superior to, 2 times than ULN, e.g. before initiating BAF-312 treatment)

Patients who have heart disorders refers to one or more disorders selected from high-grade AV block, sick sinus syndrome, ischemic heart disease, congestive heart failure, and arrhythmia. For example, this concerns patients suffering from or at risk of bradyarrhythmia, patients with high grade atrioventricular blocks or sick sinus syndrome, patients with a history of syncopal episodes, or patients under beta blockers or anti-arrhythmic treatment, such as patients under anti-arrhythmic drugs.

According to the present application, there is provided a specific monitoring of patients treated with a S1P receptor modulator or agonist, e.g. BAF-312, a phosphate derivative thereof or a pharmaceutically acceptable salt thereof, wherein said patients are suffering from an inflammatory or an autoimmune disease or disorder. e.g. multiple sclerosis, comprising any ones of the following steps of:
   i) observation period, e.g. at least 6 hour, e.g. 4 to 6 hours, during which or at the end of which heart rate is checked, as defined herein,
   ii) annual skin examination after first dose administration, as defined herein,
   iii) regular review of liver enzyme, e.g. serum ALT, as defined herein,
   iv) ophthalmologic examinations 2 to 12 months, e.g. 3 to 4 months, after first dose administration, as defined herein,
   v) regular checking of patient visual function, as defined herein.

There is further provided method of administering a S1P receptor modulator or agonist, e.g. Siponimod in the form of BAF-312, a phosphate derivative thereof or a pharmaceutically acceptable salt thereof, to patients suffering from an inflammatory or an autoimmune disease or disorder, e.g. multiple sclerosis, comprising
  a) performing any ones of the following steps of:
   i) observation period, e.g. at least 6 hour, e.g. 4 to 6 hours, during which or at the end of which heart rate is checked, as defined herein,
   ii) annual skin examination after first dose administration, as defined herein,
   iii) regular review of liver enzyme, e.g. serum ALT, as defined herein,
   iv) ophthalmologic examinations 3 to 4 months after first dose administration, as defined herein,
   v) regular checking of patient visual function, as defined herein; and
  b) if required, interrupting Siponimod administration based upon the results of one of more of the above steps or changing the treatment regimen and/or administering a second drug. Step b) may correspond to appearance of adverse events. The second drug may be a drug which mitigates said possible adverse events.

Interrupting Siponimod administration, changing the treatment regimen and/or administering a second drug, may occur in case of any of the following conditions: bradycardia or atrioventricular conduction abnormalities, macular edema or other visual disturbance, skin cancer, altered liver functions or liver injury, infections or hypertension. Duration of the interruption is defined by the physician.

Interrupting Siponimod administration, changing the treatment regimen and/or administering a second drug, may also occur in case the lymphocyte count of the patient becomes abnormally low, or becomes lower than 2001 mL.

For example, step a) may comprise one or more steps of
   i) monitoring the heart rate of the patient,
   ii) monitoring infections or infestations, e.g. viral infections, and
   iii) performing ophthalmologic examination within the first 1 to 10 after starting administration.

Therapeutic Dosages

In a preferred embodiment of the present application the methods for administering BAF-312, a phosphate derivative thereof or a pharmaceutically acceptable salt thereof as defined herein above, in particular the methods for treating an inflammatory or autoimmune disease or disorder, limiting the symptoms associated thereof or the progression thereof, e.g. multiple sclerosis, in a patient in need thereof comprise administering a daily dosage of BAF-312, a phosphate derivative thereof or a pharmaceutically acceptable salt thereof, e.g. BAF-312 hydrochloride, of not more than 2 mg, e.g. of about 2 mg.

According to the present application there is provided a compound selected from Siponimod (BAF-312), a phosphate derivative thereof or a pharmaceutically acceptable salt thereof, e.g. Siponimod hydrochloride, for use in treating or preventing an inflammatory or autoimmune disease, whereby said compound is administered in such a way to a patient that the adverse events possibly associated with administration of said compound are controlled, limited, reduced or abolished. For example, the daily dosage of Siponimod (BAF-312), a phosphate derivative thereof or a pharmaceutically acceptable salt thereof, e.g. Siponimod hydrochloride, does not exceed 2 mg, e.g. is of about 2 mg.

In a specific embodiment of the present application there is provided a method for treating multiple sclerosis, controlling or limiting the symptoms associated thereof or reducing the severity of said disease in a patient in need thereof, comprising administering a daily dosage of Siponimod (BAF-312), a phosphate derivative thereof or a pharmaceutically acceptable salt thereof, e.g. Siponimod hydrochloride, wherein said daily dosage does not exceed 2 mg, e.g. is of about 2 mg, and wherein the patient is further affected by asthma (for example moderate asthma), by a disease or disorder impacting eyes or has an history of eyes diseases or disorders (for example is affected by uveitis or diabetes), show high-grade AV block, sick sinus syndrome, hepatic dysfunction or hypertension.

In a further embodiment of the present application there is provided a method for treating multiple sclerosis, controlling or limiting the symptoms associated thereof or reducing the severity of said disease in a patient in need thereof, comprising administering a daily dosage of Siponimod (BAF-312), a phosphate derivative thereof or a pharmaceutically acceptable salt thereof, e.g. Siponimod hydrochloride, wherein said daily dosage does not exceed 2 mg, e.g. Is of about 2 mg, and wherein the patient is pregnant.

In yet a further embodiment of the present application there is provided a method for treating multiple sclerosis, limiting the symptoms associated thereof or reducing the severity of said disease in a patient in need thereof, comprising administering a daily dosage of Siponimod (BAF-312), a phosphate derivative thereof or a pharmaceutically acceptable salt thereof, e.g. Siponimod hydrochloride, wherein said daily dosage does not exceed 2 mg, e.g. is of about 2 mg, and wherein the patient is a MS patients who has never received treatment for MS, e.g. do novo patient.

According to the present application, adopting the treatment regimen may consist of decreasing the dosage, or increasing the time between two consecutive administrations of the S1P receptor modulator or agonist, e.g. Siponimod, a phosphate derivative thereof or a pharmaceutically acceptable salt thereof. For example, it may consist of administering 0.25 mg of Siponimod, a phosphate derivative thereof or a pharmaceutically acceptable salt thereof, two times a day. It may also consist of increasing stepwise the dosage of the drug during the first period of administration up to a daily dosage of 2 mg or 1 mg, e.g. adopting a stepwise administration, e.g. a titration.

The present application pertains to a method for treating multiple sclerosis comprising
(a) administering a varied dose of a drug selected from the group consisting of Siponimod (BAF-312), a phosphate derivative thereof or a pharmaceutically acceptable salt thereof in a patient in need thereof,
(b) monitoring adverse events occurring in said patient,
(c) monitoring reduction or abolition of symptoms associated with multiple sclerosis, and
(d) determining optimal dose for said patient The daily dose of the drug may be not exceeding 2 mg.

In another embodiment, the daily dose of the drug is above 2 mg, e.g. is about 3.00 mg, e.g. about 4.00 mg, e.g. about 5.00 mg.

There is also provided a S1P receptor modulator or agonist, e.g. BAF-312, a phosphate derivative thereof or a pharmaceutically acceptable salt thereof, for use in a method for treating an inflammatory or autoimmune disease, e.g. multiple sclerosis, wherein said method comprises
(a) administering a varied dose of said S1P receptor modulator or agonist in a patient in need thereof,
(b) monitoring adverse events occurring in said patient,
(c) monitoring reduction or abolition of symptoms associated with said inflammatory or autoimmune disease, and
(d) determining optimal dose for said patient.

This method is particularly adapted for BAF-312, a phosphate derivative thereof or a pharmaceutically acceptable salt thereof, e.g. BAF-312 hydrochloride, for treating multiple sclerosis.

When the S1P receptor modulator or agonist is selected from BAF-312, a phosphate derivative thereof or a pharmaceutically acceptable salt thereof, e.g. is BAF-312 hydrochloride, and the disease is multiple sclerosis, the daily dose of the drug may not be exceeding 2 mg.

In another embodiment, the S1P receptor modulator or agonist is selected from BAF-312, a phosphate derivative thereof or a pharmaceutically acceptable salt thereof, e.g. BAF-312 hydrochloride, and the daily dose is exceeding 2 mg, e.g. is about 3 mg, e.g. about 4 mg, e.g. about 5 mg.

In yet a further embodiment of the present application, there is provided a personalized method for treating an inflammatory or autoimmune disease or disorder, e.g. multiple sclerosis, in a patient in need thereof comprising administering to said patient a therapeutically effective amount of a S1P receptor modulator or agonist,
wherein said method comprises
(a) administering a varied dose of said drug to the patient,
(b) monitoring adverse events occurring in said patient,
(c) monitoring reduction or abolition of symptoms associated with multiple sclerosis, and
(d) determining optimal dose for said patient,
wherein said regimen is adapted for treating said disease or disorder and controlling, reducing, or abolishing the possible adverse events associated with administering said S1P receptor modulator or agonist.

The steps (a) to (d) above may also be used in a method for determining a personalized therapeutic treatment regimen of a drug selected from the group consisting of Siponimod (BAF-312), a phosphate derivative thereof or a pharmaceutically acceptable salt thereof, in a patient suffering from an inflammatory or autoimmune disease, e.g. multiple sclerosis.

The present application also pertains a compound selected from BAF-312, a phosphate derivative thereof or a pharmaceutically acceptable salt thereof, e.g. BAF-312 hydrochloride, for use in a method for treating an inflammatory or autoimmune disease or disorder in a patient in need thereof, wherein said method is personalized, e.g. is adapted for treating said disease or disorder to the specific profile of the patient in such a way that the adverse events associated with administering said S1P receptor modulator or agonist are controlled, reduced, or abolished. In such a case, the patient to be treated may be selected from patients who have never received treatment for that disease or disorder, patients suffering or at risk of heart failure or arrythmias, patients affected by asthma, patients who have eyes diseases or disorders, hepatic dysfunction or hypertension.

The present application provides for a compound selected from BAF-312, a phosphate derivative thereof or a pharmaceutically acceptable salt thereof, e.g. BAF-312 hydrochloride, for use in treating patients suffering from an inflammatory or an autoimmune disease or disorder, e.g. multiple sclerosis, wherein the compound is administered through the administration pattern defined above.

The present application also provides for a compound selected from BAF-312, a phosphate derivative thereof or a pharmaceutically acceptable salt thereof, e.g. BAF-312 hydrochloride, for use in treating patients suffering from an inflammatory or an or disorder disease, e.g. multiple sclerosis, wherein the compound is administered through the patient monitoring defined above.

Combination

In another embodiment of the present application, the S1P receptor modulator, e.g. Siponimod (BAF-312), a phosphate derivative thereof or a pharmaceutically acceptable salt thereof, e.g. Siponimod hydrochloride, is administered together with a second drug which mitigates the possible adverse event associated with administration of Siponimod.

Such a second drug may be administered only in the event that an adverse event, e.g. a side-effect, occurs or increases in intensity or frequency to a level which is not acceptable anymore, e.g. as hereinabove described.

The second drug may be selected from the group consisting of drugs which treat or prevent macular edema, anti-cancer agents (e.g. chemotherapeutic agents), anti-infection agents, anti-hypertensive drugs, anti-bradychardia agents, and mixture thereof.

Examples of second drug include, but are not limited to, calcium channel blocker (e.g. diltiazem), atenolol, valsartan, When the S1P receptor modulator or agonist of the present application, e.g. Siponimod (BAF-312), a phosphate derivative thereof or a pharmaceutically acceptable salt thereof, e.g. Siponimod hydrochloride, is administered together with a second drug which mitigates the possible adverse event associated with administration of Siponimod, the daily dosage of said S1P receptor modulator or agonist may be above 2 mg, e.g. may be about 3 mg, e.g. about 4 mg, e.g. about 5 mg.

For example there is provided a combination, e.g. a kit, containing a S1P receptor modulator or agonist of the present application, e.g. Siponimod (BAF-312), a phosphate derivative thereof or a pharmaceutically acceptable salt thereof, e.g. Siponimod hydrochloride, and a second drug which is selected from the group consisting of anti-cancer agents, anti-infection agents, anti-microbial agents, anti-viral therapy, and anti-hypertensive drugs, whereby the dosage of said S1P receptor modulator or agonist is above 2 mg, e.g. is about 3 mg or about 4 mg or about 5 mg or about 6 mg.

The present application also provides a specific dosage regimen of BAF-312 for treating an inflammatory or autoimmune disease or disorder, limiting the symptoms associated thereof or the progression thereof, e.g. multiple sclerosis, in a patient in need thereof, comprising administering to said patient a daily dosage of Siponimod (BAF-312), a phosphate derivative thereof or a pharmaceutically acceptable salt thereof, which leads to a reduction of peripheral lymphocyte count of about 70 to 75%, e.g. of about 73%, 75% or 76%.

In another embodiment the present application provides a specific dosage regimen of BAF-312 for treating an inflammatory or autoimmune disease or disorder, limiting the symptoms associated thereof or the progression thereof, e.g. multiple sclerosis, in a patient in need thereof, comprising administering to said patient a daily dosage of Siponimod (BAF-312), a phosphate derivative thereof or a pharmaceutically acceptable salt thereof, which leads to a reduction of peripheral lymphocyte count to a level low enough to obtain the therapeutic effect on the disease while controlling, limiting or abolishing the incidence of infections. Preferably this daily dosage is not more than 2 mg of Siponimod (BAF-312), a phosphate derivative thereof or a pharmaceutically acceptable salt thereof, e.g. of the hydrochloride salt thereof.

Utility of the dosage regimen of the present application in treating diseases and conditions as hereinabove specified may be demonstrated in standard animal or clinical tests, e.g. in accordance with the methods described hereinafter.

The invention claimed is:

1. A method for treating relapsing remitting multiple sclerosis in a patient in need thereof, the method comprising:
   (a) identifying a patient suffering from relapsing remitting multiple sclerosis at risk of contracting infection caused by varicella zoster virus by testing said patient for a history of infection caused by varicella zoster virus,
   (b) vaccinating the patient at risk of contracting infection caused by varicella zoster virus, and
   (c) administering orally Siponimod or a pharmaceutically acceptable salt thereof to said patient at a daily dosage of 2 mg,
   thereby limiting the risk of infection caused by varicella zoster virus,
   wherein the relapsing remitting multiple sclerosis is treated by the administration of Siponimod.

2. The method according to claim 1, wherein treating comprises reducing the frequency of clinical exacerbations.

3. The method according to claim 1, wherein Siponimod is administered as a hydrochloride salt.

4. The method according to claim 1, wherein the infection is chickenpox.

5. A method for treating multiple sclerosis in a patient in need thereof, the method comprising:
   (a) identifying a patient suffering from multiple sclerosis at risk of contracting infection caused by varicella zoster virus by testing said patient for a history of infection caused by varicella zoster virus,
   (b) vaccinating the patient at risk of contracting infection caused by varicella zoster virus, and
   (c) administering orally a therapeutically effective amount of Siponimod or a pharmaceutically acceptable salt thereof to said patient,
   thereby limiting the risk of infection caused by varicella zoster virus,
   wherein the multiple sclerosis is treated by the administration of Siponimod.

6. The method of claim 5, wherein the multiple sclerosis is primary progressive multiple sclerosis.

7. The method of claim 5, wherein the Siponimod is administered in a dosage of 0.25 mg twice per day.

8. The method of claim 5, wherein the Siponimod is administered in a dosage of 2 mg per day.

* * * * *